US011986266B2

(12) United States Patent
Tearney et al.

(10) Patent No.: US 11,986,266 B2
(45) Date of Patent: May 21, 2024

(54) SPECKLE-BASED IMAGE DISTORTION CORRECTION FOR LASER SCANNING MICROSCOPY

(71) Applicant: THE GENERAL HOSPITAL CORPORATION, Boston, MA (US)

(72) Inventors: Guillermo J. Tearney, Cambridge, MA (US); Jiheun Ryu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 264 days.

(21) Appl. No.: 17/310,263

(22) PCT Filed: Jan. 27, 2020

(86) PCT No.: PCT/US2020/015153
§ 371 (c)(1),
(2) Date: Jul. 27, 2021

(87) PCT Pub. No.: WO2020/159844
PCT Pub. Date: Aug. 6, 2020

(65) Prior Publication Data
US 2022/0054013 A1    Feb. 24, 2022

Related U.S. Application Data

(60) Provisional application No. 62/797,548, filed on Jan. 28, 2019.

(51) Int. Cl.
*G02B 27/48* (2006.01)
*A61B 5/00* (2006.01)
*G01N 21/47* (2006.01)

(52) U.S. Cl.
CPC .......... *A61B 5/0066* (2013.01); *A61B 5/7207* (2013.01); *A61B 5/7275* (2013.01);
(Continued)

(58) Field of Classification Search
CPC ............ G01N 2021/479; A61B 5/0066; A61B 5/7203; A61B 5/7207; G02B 27/48
See application file for complete search history.

(56) References Cited

U.S. PATENT DOCUMENTS

| 4,792,231 A | 12/1988 | Fried |
| 7,878,651 B2 | 2/2011 | O'Hara et al. |

(Continued)

FOREIGN PATENT DOCUMENTS

| CN | 102119326 A | 7/2011 |
| CN | 107260195 A | 10/2017 |

(Continued)

OTHER PUBLICATIONS

Dafei Huang, "Applying Detection Proposals to Visual Tracking for Scale and Aspect Ratio Adaptability" Dec. 26, 2016 (Year: 2016).*

(Continued)

*Primary Examiner* — Maurice C Smith
(74) *Attorney, Agent, or Firm* — Quarles & Brady LLP

(57) ABSTRACT

A method of correcting distortion of an image, including: analyzing, by a processor, an image segment of the image to identify a speckle artifact, the image segment being obtained from a scanning imaging device; determining, by the processor, an aspect ratio of a shape of the speckle artifact; determining, by the processor, a correction factor for the shape of the speckle artifact based on the aspect ratio; and adjusting, by the processor, a dimension of the image segment based on the correction factor.

34 Claims, 11 Drawing Sheets

(52) U.S. Cl.
CPC ......... *G01N 21/4788* (2013.01); *G02B 27/48* (2013.01); *G01N 2021/479* (2013.01)

(56) References Cited

U.S. PATENT DOCUMENTS

| | | |
|---|---|---|
| 2005/0100245 A1 | 5/2005 | Chen et al. |
| 2008/0262359 A1 | 10/2008 | Tearney et al. |
| 2011/0013002 A1 | 1/2011 | Thompson et al. |
| 2013/0245456 A1 | 9/2013 | Ferguson, Jr. et al. |
| 2014/0378846 A1 | 12/2014 | Hosoda et al. |
| 2015/0216415 A1 | 8/2015 | Uribe-Patarroyo et al. |
| 2016/0328848 A1 | 11/2016 | Andre et al. |
| 2017/0140560 A1 | 5/2017 | Kraus et al. |
| 2017/0143213 A1 | 5/2017 | Nadkarni |
| 2020/0304755 A1* | 9/2020 | Narayan .............. G06V 40/168 |

FOREIGN PATENT DOCUMENTS

| | | |
|---|---|---|
| CN | 107735015 A | 2/2018 |
| CN | 108573468 A | 9/2018 |
| JP | 2020064564 A * | 4/2020 |

OTHER PUBLICATIONS

Saudi Arabia Patent Office, First Examination Report, Application No. 521422655, dated Mar. 13, 2023, 8 pages [no English language translation available].

International Search Report and Written Opinion issued in corresponding PCT Application No. PCT/US2020/015153, dated May 22, 2020.

International Preliminary Report on Patentability issued in corresponding PCT Application No. PCT/US2020/015153, dated Jul. 27, 2021.

European Patent Office, Communication, Extended Search Report, Application No. 20748254.8, dated Oct. 17, 2022, 4 pages.

Japan Patent Office, Notification of Reasons for Refusal, Application No. 2021-543361, Dec. 12, 2023, 4 pages.

The State Intellectual Property Office of People's Republic of China, First Office Action and Search Report, Application No. 202080025783.2, Jan. 9, 2024, 10 pages.

European Patent Office, Partial Search Report, Application No. 23219093.4, Mar. 19, 2024, 12 pages.

* cited by examiner

SPECKLE-BASED IMAGE DISTORTION CORRECTION FOR LASER SCANNING MICROSCOPY

CROSS-REFERENCE TO RELATED APPLICATIONS

This application is a U.S. National Stage of International Application No. PCT/US2020/015153 filed Jan. 27, 2020 which is based on, claims the benefit of, and claims priority to U.S. Provisional Patent Application No. 62/797,548 filed on Jan. 28, 2019, which is hereby incorporated herein by reference in its entirety for all purposes.

STATEMENT REGARDING FEDERALLY SPONSORED RESEARCH

This invention was made with government support under grant number R01DK091923 awarded by the National Institutes of Health. The government has certain rights in the invention.

BACKGROUND

Image distortion caused by non-uniform laser scanning may be a challenge for certain laser scanning imaging devices such as those used in catheter endoscopy and capsule endoscopy. For example, parts related to rotation or scanning may have a certain amount of friction and this friction may vary during rotation, e.g. depending on the orientation of the imaging device or the waveform of scanning. As this friction is generally unknown and unpredictable, the distortion caused by the friction may end up residing in the image data that is generated, e.g. as geometric distortions of the sample.

SUMMARY

Disclosed herein are methods and systems for correction of distortion of images from an image probe, including techniques for measuring and correcting image distortion based on a shape and/or size of speckles or other features that appear in the images.

In various embodiments, the methods and systems may include one or more of the following:
1) Determining the scanning speed based on the speckle shape and/or size;
2) Calculating the speckle shape and/or size based on auto-covariance of the image, e.g. after the image has been filtered by a high-pass filter;
3) Performing calibrations to adjust for a nonlinear relation between a rate of movement (e.g. rotational or linear) of the imaging probe compared to the speckle shape and/or size; or
4) Aligning each of a number of distortion-compensated lines by minimizing a cross-correlation.

These correction techniques may be adopted by any imaging devices that have rotational and/or linear scanning parts. These techniques may be implemented in software to measure the amount of distortion, thus products that encompass embodiments of the disclosed methods and systems may be simpler and more cost-effective and produce more robust results.

In one embodiment, the invention includes a method of correcting distortion of an image, including: analyzing, by a processor, an image segment of the image to identify a speckle artifact, the image segment being obtained from a scanning imaging device; determining, by the processor, an aspect ratio of a shape of the speckle artifact; determining, by the processor, a correction factor for the shape of the speckle artifact based on the aspect ratio; and adjusting, by the processor, a dimension of the image segment based on the correction factor.

In another embodiment, the invention includes an apparatus for correcting distortion of an image, including: a processor; and a memory in communication with the processor having stored thereon a set of instructions which, when executed by the processor, cause the processor to: analyze an image segment of the image to identify a speckle artifact, the image segment being obtained from a scanning imaging device, determine an aspect ratio of a shape of the speckle artifact, determine a correction factor for the shape of the speckle artifact based on the aspect ratio, and adjust a dimension of the image segment based on the correction factor.

In yet another embodiment, the invention includes a method of distortion correction, the method including: providing an image; dividing the image into a plurality of substantially parallel strips, each strip extending in a first direction; dividing each strip into a plurality of substrips along a second direction substantially perpendicular to the first direction; analyzing each of the plurality of substrips to locate at least one locally bright feature; adjusting at least a portion of each substrip to urge the at least one locally bright feature toward a predetermined shape to create a corrected substrip; reassembling the plurality of corrected sub strips into a corrected strip; and reassembling the plurality of corrected strips into a corrected image.

In still another embodiment, the invention includes an apparatus for correcting distortion of an image, including: a scanning imaging device including a coherent light source, the scanning imaging device being configured to obtain an image of a sample; a processor in communication with the scanning imaging device; and a memory in communication with the processor having stored thereon a set of instructions which, when executed by the processor, cause the processor to: analyze an image segment of the image to identify a speckle artifact, determine an aspect ratio of a shape of the speckle artifact, determine a correction factor for the shape of the speckle artifact based on the aspect ratio, and adjust a dimension of the image segment based on the correction factor.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

In accordance with some embodiments of the disclosed subject matter, mechanisms (which can include systems, methods, and media) for image distortion correction are provided.

Laser speckle, which in some instances may be considered to be an unwanted artifact, may be used to advantage is various disclosed embodiments by using the laser speckle spots, which are expected to be substantially circular, to determine the amount and orientation of any distortion that may have occurred in an image based on the degree to which the speckles deviate from a substantially circular shape. In various embodiments, the features that are used in the disclosed procedures to compensate for distortion and features that have a particular localized brightness, such as laser speckles, and which are readily discerned using the automated procedures disclosed herein. While these features are referred to herein as laser speckles, these features may have other origins as well but are nevertheless useful for identifying and correcting for image distortion.

In many imaging use environments (e.g., capsule endoscopy using an illuminating laser) undesirable distortion artifacts may occur. For example, in a 360° rotation capsule endoscopy use environment, the motor rotating the illuminating laser and/or image-receiving sensor may stick and/or slip. In that case, since the rotation is not accomplished smoothly, distortion in the recorded image may occur because image reconstruction from scanning data is based on an assumption that the scanned data points are equally spaced. That is, a series of data points are collected as the imaging probe is rotated and/or translated through a specimen. For a helical scan which is obtained when the probe is simultaneously rotated and translated through a luminal sample, an image of the sample is generated by assembling the series of data points into a two- or three-dimensional representation based on an assumption that the probe rotates and translates at uniform rates. However, friction within the device (e.g. friction within the motor itself or friction between a rotating optical fiber and a sheath which houses the fiber, among various possible sources) may give rise to sticking or slippage that can cause non-uniform movement which in turn give rise to distortions in the images that are generated from the data stream.

Thus, the present distortion correction methods and systems make use of naturally-occurring speckles from the illuminating laser to determine how much distortion in the scanning direction has occurred and accordingly modifying the image to account for and compensate for that distortion.

Figure 1:
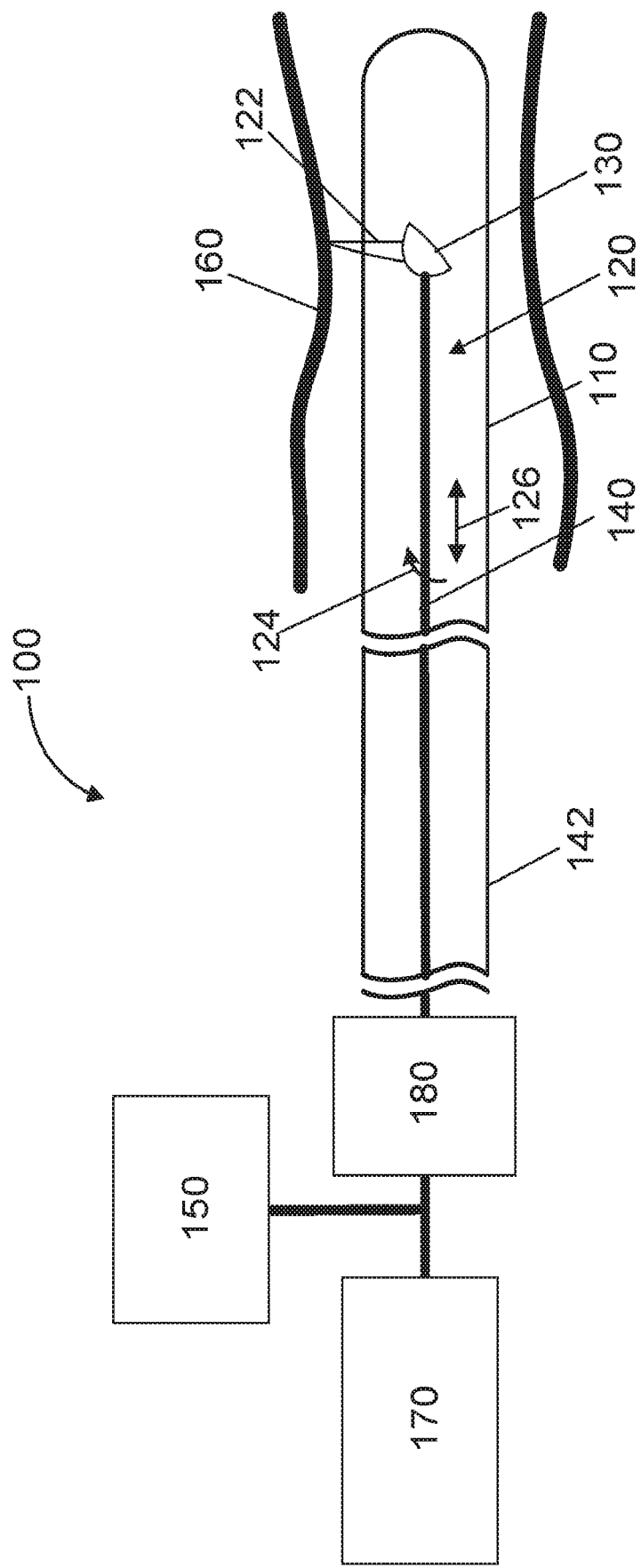
FIG. 1 shows an example system that may be used to collect data for use with embodiments of the methods and systems disclosed herein.

FIG. 1 shows an example system 100 that may be used to collect data for use with embodiments of the methods and systems disclosed herein. System 100 includes a catheter 110 having an optical probe 120 disposed therein which includes a reflector 130 (e.g. a ball lens, as shown, or a prism or mirror) at the end of a waveguide 140 (e.g. an optical fiber). A light source 150 provides illumination to the waveguide 140 which transmits the light to the reflector 130 of the optical probe 120 which directs a beam 122 to a sample 160 (e.g. a luminal tissue such as a blood vessel or a portion of the GI tract). Light from the sample 160 returns along the path to an image collection and processing system 170 which collects and processes the returned light to form images or other data. The light source 150 is a coherent light source such as a laser, which gives rise to the speckle artifacts that are used in the present procedures to make image corrections.

The optical probe 120 may be rotated 124 and/or translated 126 during data collection in order to collect data from a full circumferential area of the sample 160 (due to rotation 124) as well as along the axial length of the sample 160 (due to translation 126). The waveguide 140 may rotate 124 and/or translate 126 within a sheath 142 before it reaches the catheter 110. To facilitate rotation and translation of the optical probe 120, a rotation and translation device 180 (which may also include a rotating optical coupler) is attached to the proximal end of the catheter. The rotation and translation device 180 may include a linear motor for translating the optical probe 120 as well as a motor (e.g. hollow core motor) for rotating the optical probe 120. In some embodiments, instead of a catheter 110, the optical probe 120 may be housed in a capsule device that the patient swallows, particularly for probing the GI tract. In various embodiments, the motor for rotating the reflector 130 may be located at the distal end adjacent to the reflector 130, particularly in capsule-based embodiments. In various embodiments, the optical probe 120 may rotate at rates of 1-30 Hz, 1-100 Hz, 1-1000 Hz, or 1-10,000 Hz, and may translate at rates of 1-10 mm/min.

In various embodiments, components that may give rise to image distortions include sticking or slippage of the waveguide 140 within the sheath 142 or catheter 110 and/or sticking or slippage of the components within the rotation and translation device 180 such as the rotational or linear/translational motors. In certain embodiments the correction procedures disclosed herein may be performed after the data has been collected, for example at a later date by processing previously-stored data. In other embodiments the correction procedures may be performed in tandem with data collection, for example by processing the data as it is collected and storing the corrected version of the data. In particular embodiments the correction procedures may be performed at substantially the same rate as data collection so that the processing is effectively in real time.

Figure 2:
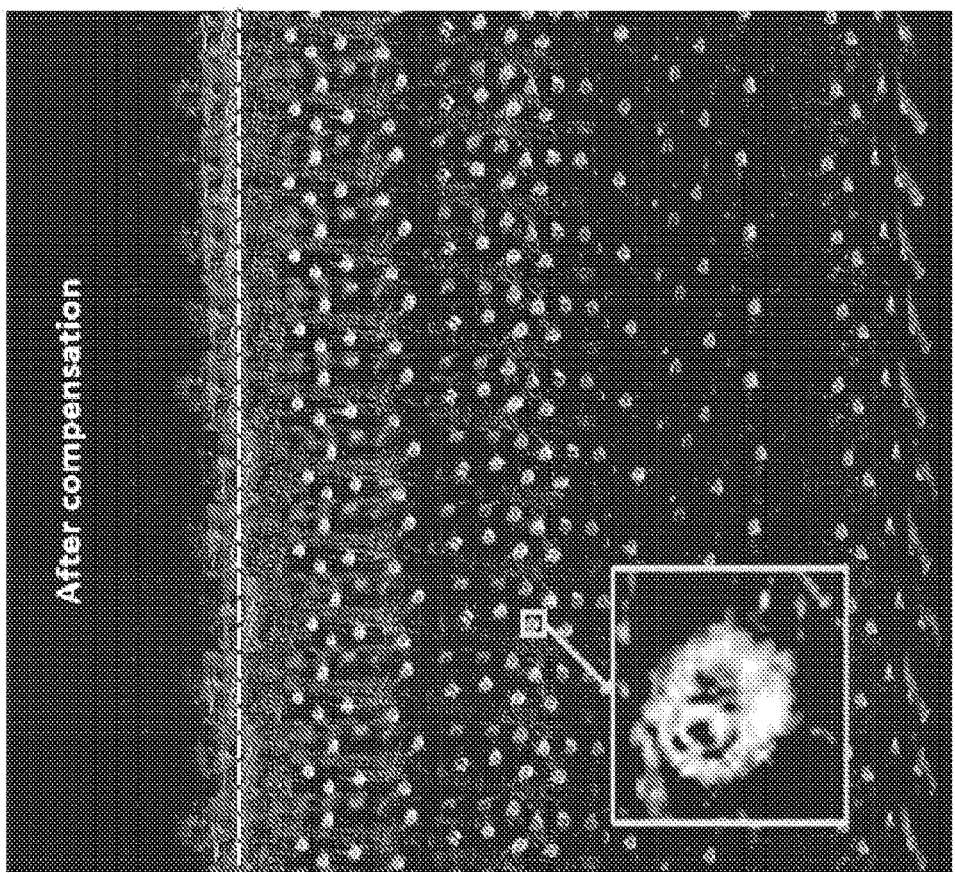
FIG. 2 shows an example of a speckle before (left panel, inset) and after (right panel, inset) distortion compensation according to embodiments disclosed herein.
Figure 2:
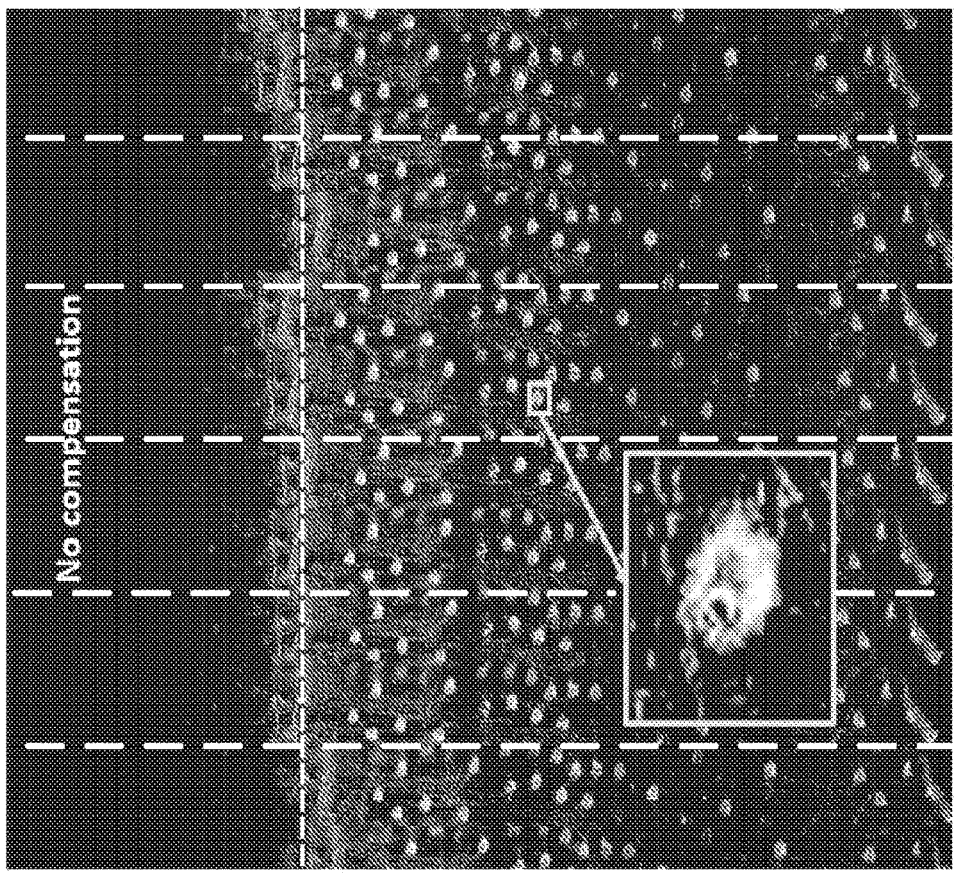

FIG. 2 shows an example of a speckle before (left panel, inset) and after (right panel, inset) distortion compensation according to embodiments disclosed herein. In various embodiments, the entire image (shown in un-corrected form in the left panel of FIG. 2) may first be divided up into small strips. For example, in some embodiments the image may be divided into strips having a first dimension (e.g. the horizontal dimension in FIG. 2) which may be in a range of 300-500 pixels (and more specifically 400 pixels in particular embodiments) and a second, substantially orthogonal dimension which may be determined by a dimension of the original image, for example a "width" of the original image; the width of the image (e.g. the vertical dimension in FIG. 2) may correspond to a direction of movement (e.g. rotation) and in particular may correspond to data collected from a complete revolution of a rotating imaging probe inside a luminal sample, where the image is a flattened representation of the tubular data set. FIG. 2 presumes a 360° rotation that "spirals" downward inside a lumen, e.g. a helical data set produced by rotating the imaging probe while simultaneously linearly advancing the probe, with the left side of each panel of FIG. 2 corresponding to an end of the lumen. As a result, each "strip" represents data from one full circular rotation of the imaging device (see vertical dashed lines in the left panel of FIG. 2, which show how the image may be divided into one possible set of image strips). In certain embodiments, the number and size of strips in an image may be related to the total height of the strip, e.g. so that each image is divided into substantially equal-sized strips.

Next, each "strip" may be subdivided along its length (e.g. along the vertical dimension in FIG. 2) into a plurality of substrips, or "frames." For example, each substrip could be substantially square, e.g. in the range of 300-500 pixels, and more specifically 400 pixels, "long". The number and size of substrips in a strip may be related to the total length of the strip, e.g. so that each strip is divided into substantially equal-sized substrips.

After the substrips are formed, each substrip is analyzed for areas of greater or lesser illumination, seeking, for example, "bright spots" or other features which indicate areas of laser speckle. In certain embodiments, speckles or "bright spots" are identified in an automated manner using image filtering procedures. In one particular embodiment, a high pass filtering scheme may be used, for example by taking a difference between the original image and a filtered copy of the image in which "noise" has been reduced or removed (e.g. by using an adaptive filter such as a Wiener filter), which produces a resulting image in which the speckles or "bright spots" are the only features or the predominant features.

Once one or more "bright spots" or other features within a substrip are identified, the shape of each of those "bright spots" or features is analyzed. In certain embodiments in which the size of the substrips or frames has been selected so that there is at most 1 feature such as a speckle or "bright spot" contained therein (see below), automated procedures may be used to recognize the borders of such features. For example, this may be done by mathematically identifying the x- and/or y-dimensions of any features based on the full width at half the maximum height (FWHM) of the feature. The ratio (i.e. aspect ratio) of the FWHM for the horizontal (or x-dimension) and vertical (or y-dimension) dimensions of the feature provides an indication of distortion, if any. For example, if the aspect ratio is approximately 1 then this indicates that little or no distortion is present, whereas aspect ratio values above or below 1 are an indication of distortion in the image (e.g. stretching or compression in a given direction).

In some embodiments, a procedure for identifying the aspect ratio of the features may be used which is based on calculating an autocovariance of the image data (or of the processed image data as discussed above in which speckles, "bright spots," or other features have been emphasized). This procedure can then return feature width values for the two orthogonal directions. For example, the SpeckleSize_gray( ) function in the code provided below uses autocovariance to process the substrips and returns feature width values for the two orthogonal directions which can take into account multiple speckles or other features within a given substrip. In the case where there are two or more such features within the substrip, the returned feature width values in each direction take into account the dimensions in each respective direction of all of the features, effectively providing an average for these dimensions. While in some embodiments the feature widths are determined by calculating a full width at half the maximum (FWHM), in the embodiment indicated by the code below the feature widths are determined using the widths at which the Gaussian values fall to values of 0.5 and $1/e^2$. This way of determining feature widths may provide a better idea of the size of the speckles size even when the amplitude of the Gaussian function is not unity (i.e. even if the function has not been normalized so that the amplitude equals 1.0), as would be expected for a good fit of the normalized data, but this procedure can produce unexpected trends.

Having identified the degree of distortion from the aspect ratio, the substrip is then virtually stretched and/or compressed (i.e., "un-distorted") to bring each speckle, "bright spot," or other feature back toward a substantially circular outline, thus creating a corrected substrip or frame. This analysis and distortion is repeated for each substrip of a given strip, and the corrected substrips are then recombined (e.g., "stitched together") in their original order to form a corrected strip.

In some embodiments the aspect ratio may be further adjusted before using the value to undo the distortion in the substrip or frame. For example, the "measured" aspect ratio may be adjusted to determine a "real" aspect ratio which is then applied to the substrip or frame to provide suitable adjustment to compensate for distortion. The adjustment to the measured aspect ratio may be performed using one of the curve-fitting formulas obtained in the procedures shown in FIGS. 3-5 and accompanying text (see below), or using any other suitable adjustment.

In one embodiment, the dimensions of the strips and substrips may be selected such that each substrip has, on average, at most one speckle, "bright spot," or other feature contained therein. By adjusting the strip and substrip dimensions to include at most one speckle or other feature, the adjustments for each substrip may be made on the basis of a single speckle or other feature rather than based on two or more features within a single substrip. Nevertheless, in other embodiments, dimensions of the strips and substrips may be selected to include on average two, three, four, or more speckles, "bright spots," or other features. In various embodiments, the sizes of substrips or frames are selected to be sufficiently small so that if multiple (e.g. 2, 3, 4, or more) speckles, "bright spots," or other features are contained within a single substrip or frame that these features are sufficiently close to one another that they have undergone the same or substantially the same amount of distortion, if any, so that any correction factor that is applied to the substrip or frame has an approximately equivalent effect on making all of the features have closer to a circular profile. If the substrips or frames are too large they may encompass regions that are distorted along with other regions that are not distorted, which will impact the determination of the correction factor and the degree to which the image distortion is properly compensated. In some embodiments the substrips may be processed so that they are square or approximately square, with substantially equal numbers of pixels in each dimension.

In some embodiments, the motion-based distortions may be relatively local and may arise, for example, due to slight delays of movement when the imaging probe encounters friction or due to slight speedups of movement when the imaging probe is freed up from friction (which may be referred to as intra-rotation NURD, see below). In view of the local nature of the distortions, it is possible that two adjacent substrips may need different amounts of correction, and a given sub strip that is distorted may be adjacent to a substrip that is not distorted and needs no correction at all. In addition, the distortions in a rotating imaging probe may occur primarily in the direction of rotation (which corresponds to the vertical dimension in FIG. 2). Therefore, in some embodiments the adjustments in dimensions (e.g. a change in aspect ratio) of a given substrip that are identified based on analysis of speckles, "bright spots," or other features may be made by changing (lengthening or shortening) the dimension of the substrip only in the direction of movement of the imaging probe (e.g. the vertical dimension in FIG. 2) while keeping the orthogonal dimension fixed. An advantage of this approach is that the adjusted substrips can be recombined into a single strip having a uniform width.

In certain embodiments, the motion-based distortions and/or the corrections to the image data to compensate for the distortions may give rise to discontinuities in the data between adjacent image strips (which may be referred to as inter-rotation NURD, see below). Various procedures may be applied to the data to correctly align and rejoin the image strips, including the procedure described below (e.g. in conjunction with the flowchart of FIG. 8) involving measuring cross-correlations between adjacent strips.

Each strip is split, analyzed/distorted, and recombined in a similar manner, and the plurality of corrected strips are then recombined, in their original order, to form a corrected image. An example of a corrected image is shown in the right panel of FIG. 2. Further use may then be made of the corrected image as desired.

It is contemplated that adjacent substrips of a strip, and/or adjacent strips of an image, may be cross-correlated in any desired manner such that edges of a portion of the image (e.g., an individual laser speckle) are aligned to assist with combining the corrected substrips and/or corrected strips in an accurate manner. As a simple example, if one corrected strip depicts a substantially hemicircular artifact having a known curvature to its circumference and an adjacent corrected strip depicts an oppositely facing substantially hemicircular artifact with a very similar or identical circumference, the corrected strips could be "matched up" with the hemicircular artifacts "mating" or otherwise having aligned circumferences, under a presumption that they are two portions of a singular substantially circular artifact. The corrected image may be provided, in any suitable form including in various user-perceptible forms, for further processing and/or analysis. The corrected images produced using the techniques disclosed herein may be transmitted and/or presented to a user (e.g. a researcher, an operator, a clinician, etc.) and/or may be stored (e.g. as part of a research database or a medical record associated with a subject).

Figure 3:
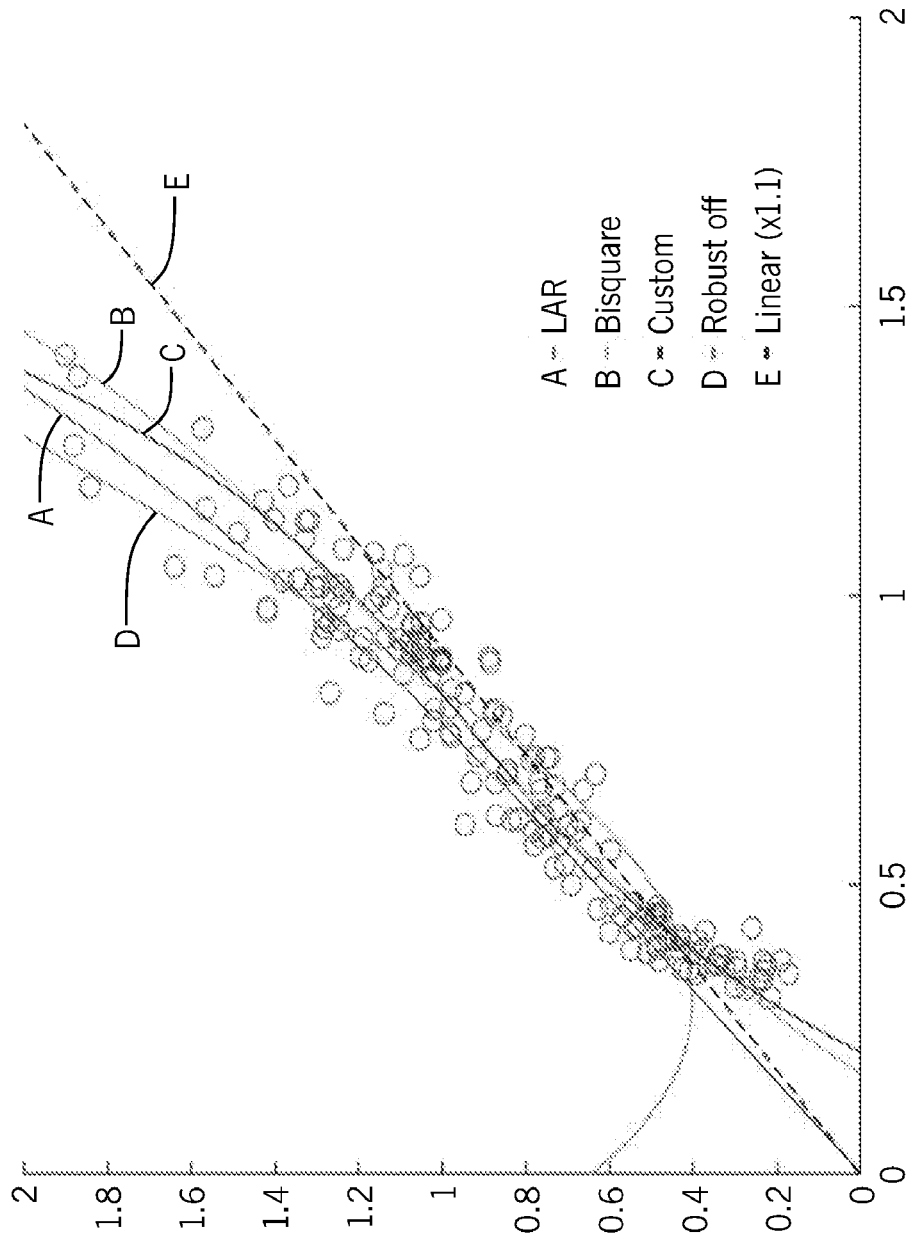
FIG. 3 represents a relationship found between image-based distortion estimation based on the speckle aspect ratio (x-axis) and the actual amount of distortion calculated by measuring the aspect ratio of spherical microbeads (y-axis, where the numbers on the axes are unitless ratios), where various curve-fitting approaches are shown superimposed over the data as part of a process for calibrating the relationship between the distortion determined using speckles and the actual distortion in the image.

To calibrate the distortion correction procedures, a series of images of fluorescent beads of different sizes were collected and analyzed (FIG. 3). This procedure was used to confirm that naturally-occurring speckles are an effective way to identify and correct for image distortion and to adjust for any deviation in the corrections that are determined using speckles to align with the distortions that are identified using a reference standard such as microbeads. The actual distortion in the images was determined based on measuring the aspect ratio of each bead, which were assumed to be spherical structures having an aspect ratio of 1; thus, any deviation from an aspect ratio of 1 for the beads was taken as an indication of actual distortion in the image. The image-based distortion was also estimated based on aspect ratio of the speckles, which are also assumed to have an aspect ratio of 1. Thus, FIG. 3 represents a relationship found between image-based distortion estimation based on the speckle aspect ratio and the actual amount of distortion calculated by measuring the aspect ratio of spherical microbeads (the axes are unitless). This relationship was used to help calibrate software for performing an example distortion correction operation.

In FIG. 3, each circle that is plotted represents an image or image portion in which the aspect ratio was determined using both microbeads and speckles, where the calculated aspect ratio for each image was graphed with the speckle-based aspect ratio on the x-axis and the microbead-based aspect ratio on the y-axis. It was determined that the aspect ratios (and hence the estimated distortions) that were generated using the two procedures were not in complete agreement and therefore several functions were used to identify the mathematical relationship between the results obtained using the two procedures. A simple linear fit of the data produces a line having a slope of 1.1 whereas other fitting procedures produced the various curves that are shown in FIG. 3. In addition to the linear fit, other procedures include least absolute residuals (LAR), Bisquare (see FIG. 4), and Robust Off (which stands for "Turning off any robust approximation," i.e. a standard least squares polynomial fitting, in contrast to LAR and Bisquare fittings). In addition, a custom curve fitting formula was determined ("Custom") based on the bisquare formula (see FIG. 5).

Figure 4:
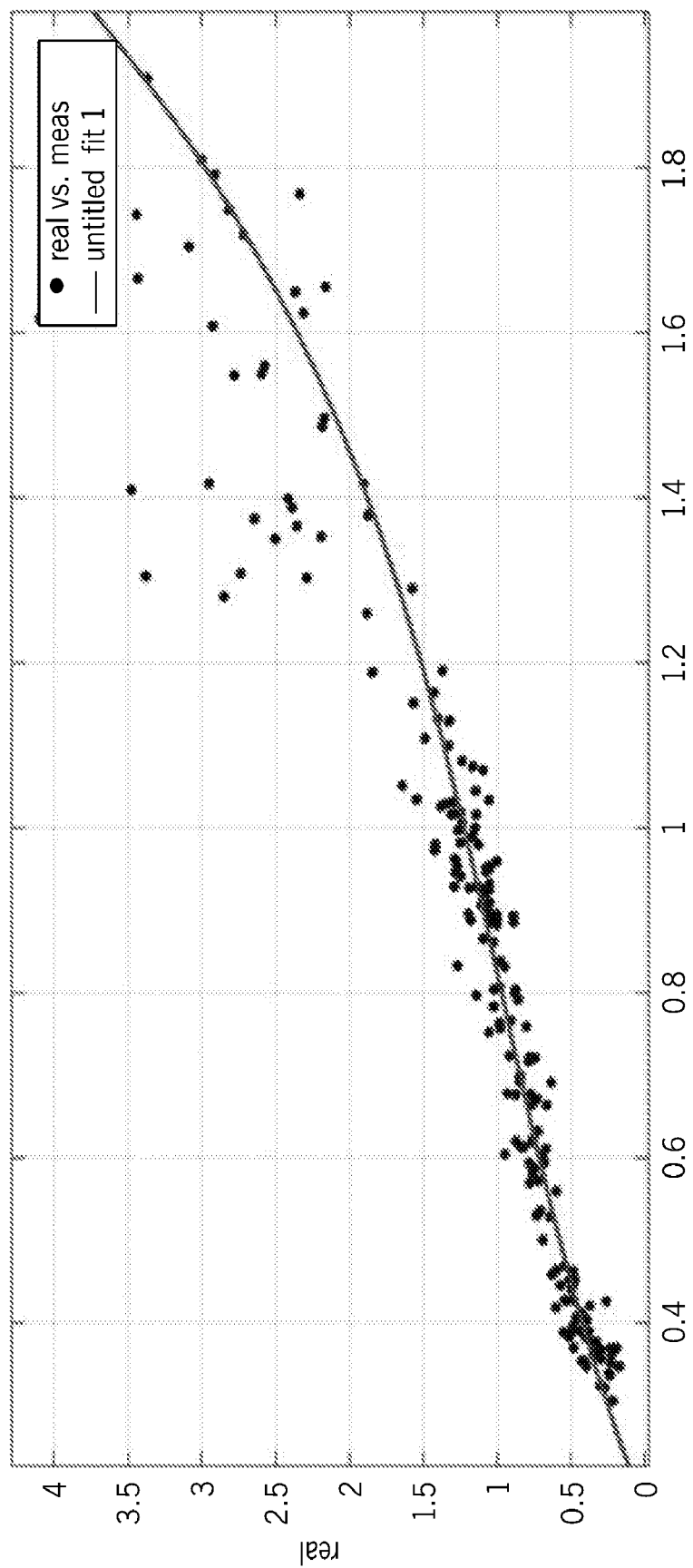
FIG. 4 represents graphed results of an analysis as in FIG. 3 in which results of a bisquare curve fitting procedure are superimposed on the data.

FIG. 4 shows a result of curve fitting of a data set using a bisquare technique using the following parameters:

$$f(x)=p1*x^3+p2*x^2+p3*x+p4$$

where the coefficients (with 95% confidence bounds) are:
p1=07736 (0.4771, 1.07)
p2=−1.865 (−2.779, −0.951)
p3=2.739 (1.896, 3.581)
p4=−0.427 (−0.6545, −0.1994)

Figure 5:
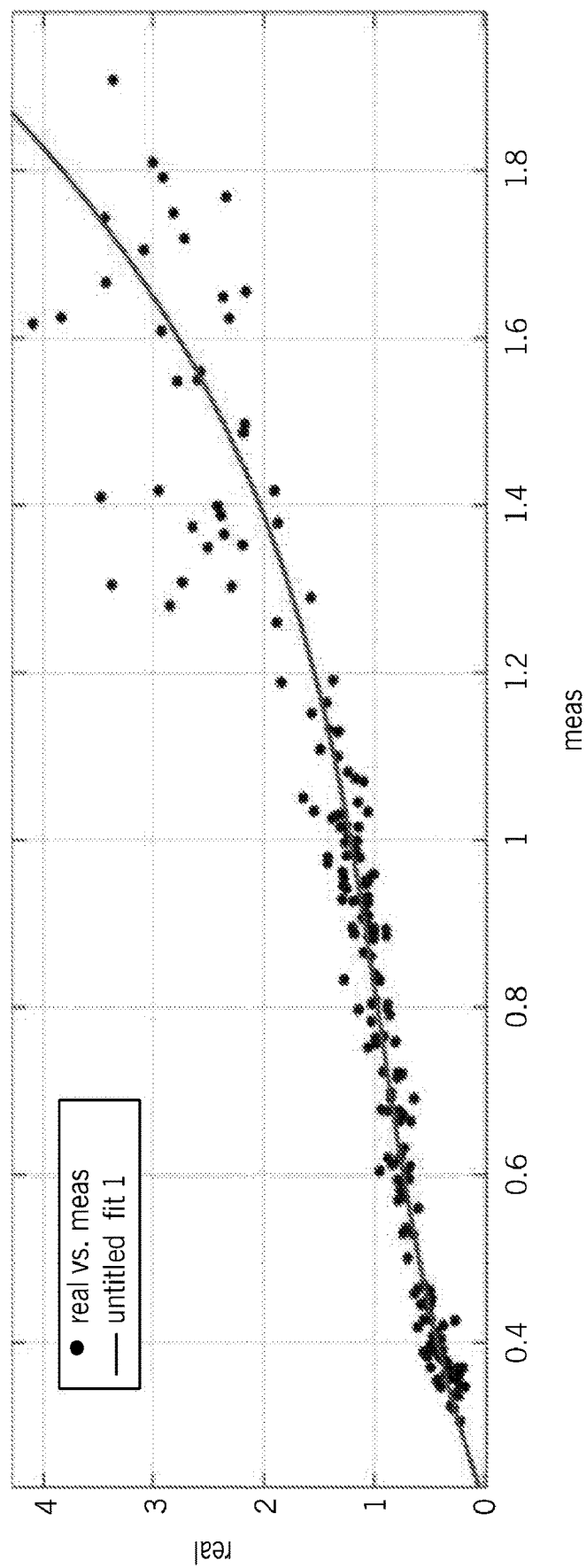
FIG. 5 represents graphed results of an analysis as in FIG. 3 in which results of a custom curve fitting procedure (based on the formula for the bisquare curve fitting procedure of FIG. 4) are superimposed on the data.

FIG. 5 shows a result of curve fitting of a data set using a custom technique using the following parameters:

$$f(x)=p1*x^3+p2*x^2+p3*x+p4$$

where the coefficients (with 95% confidence bounds) are:
p1=1.619 (1.303, 1.934)
p2=−3.786 (−4.759, −2.813)
p3=4.088 (3.191, 4.985)
p4=−0.7122 (−0.9544, −0.47)
See FIG. 4 for further information.

Figure 6:
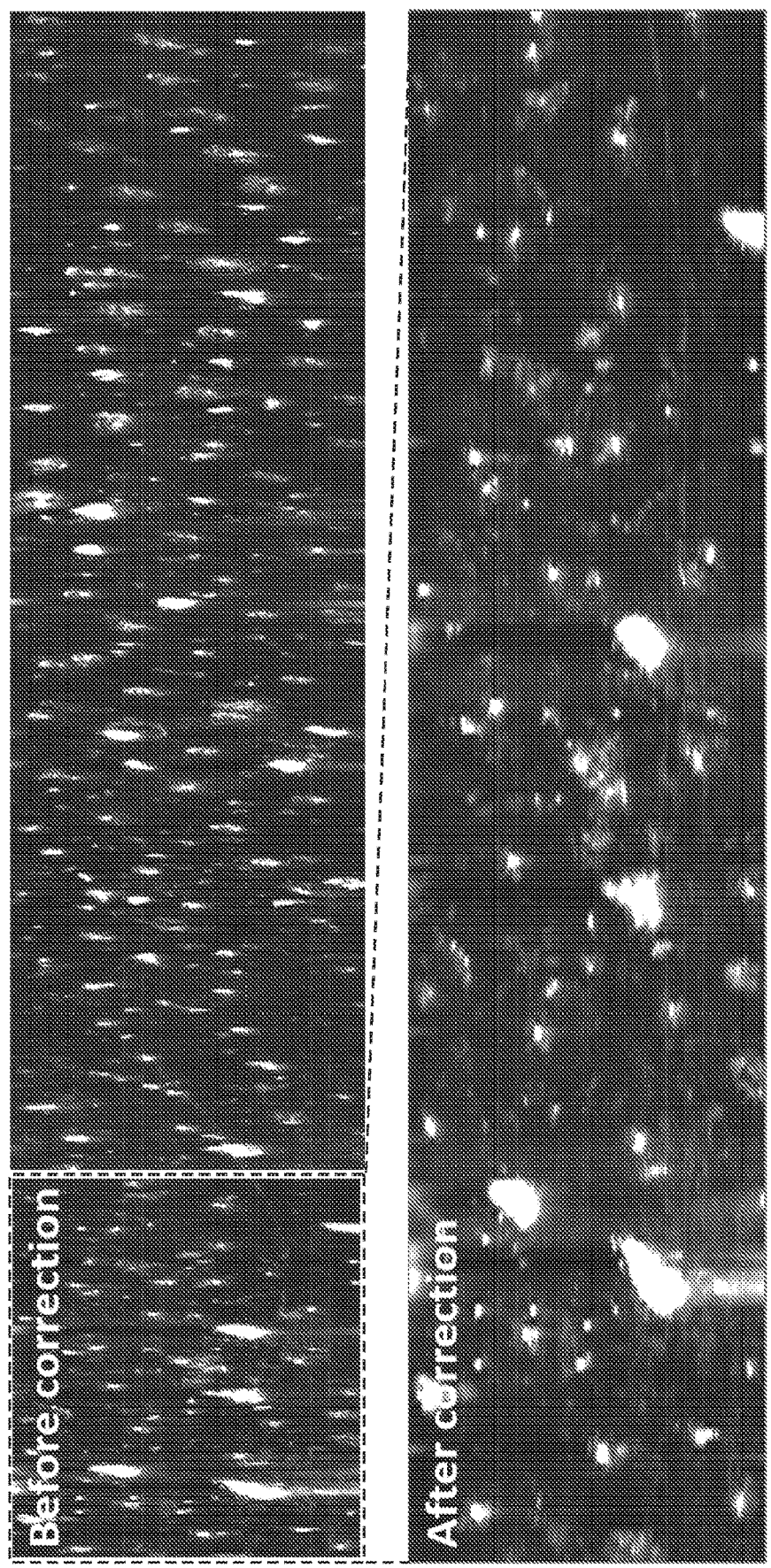
FIG. 6 shows how one substrip (the red-squared area in the top image) is adjusted to form the corrected substrip (bottom image)
Figure 7:
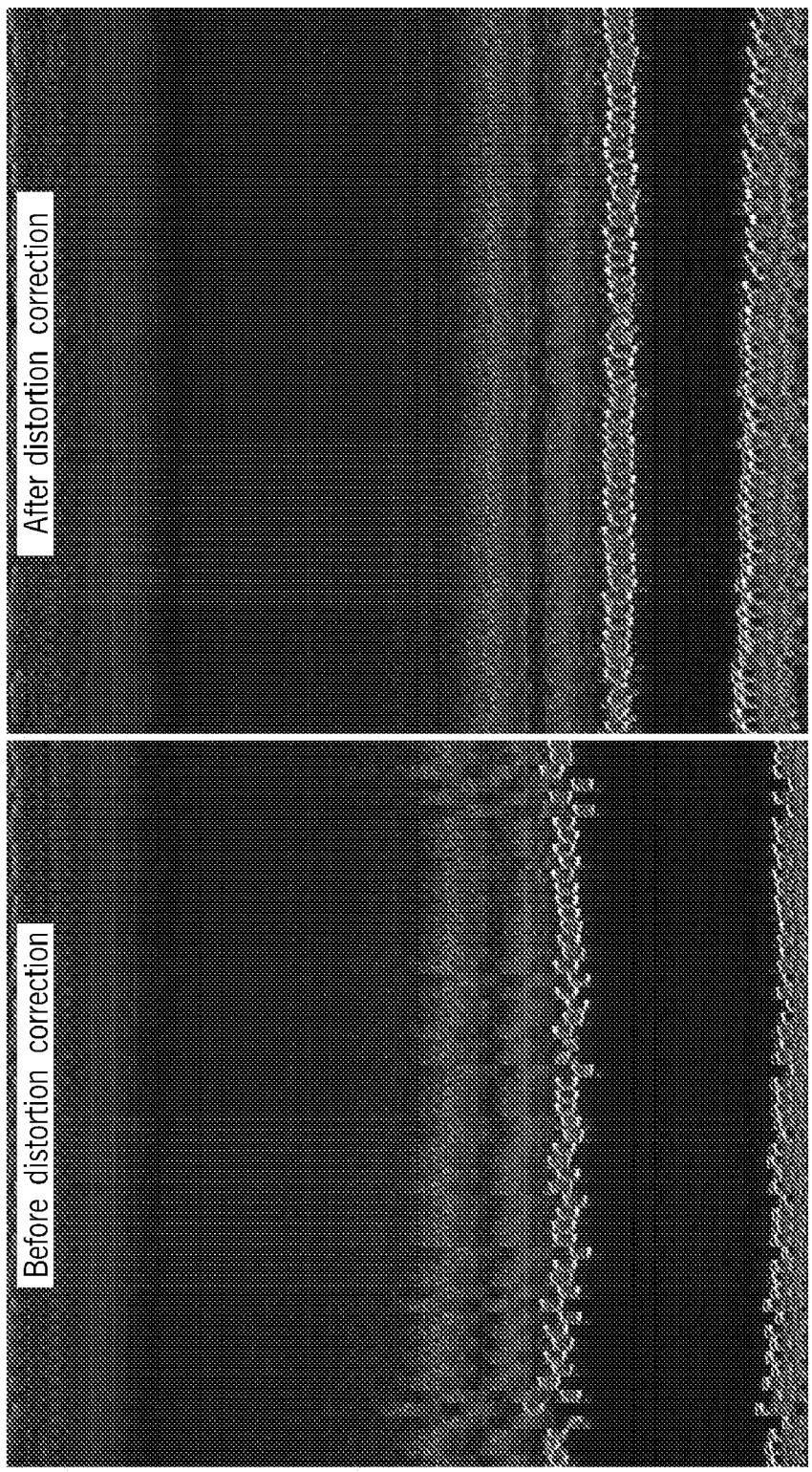
FIG. 7 depicts how a smoother, more regular image can be created using the distortion correction described herein by applying compensation in the axial scanning direction.

The test sample used to produce the images of FIGS. 6 and 7 included a set of dry microspheres that were attached to the inside walls of a vial and imaged using a capsule-based imaging device. The size of the microspheres is 50.2 μm±0.3 μm (4K-50, Thermo Scientific 3K/4K Series Particle Counter Standards). The size was selected so that the microspheres would be large enough to confirm the circular shape of each microsphere in the images but also small enough to fit within a single imaging field-of-view size, which is 200 μm×200 μm, although other size microspheres smaller than 100 µm and larger than 10 µm may also be used. The image in FIG. 7 was collected at a lower magnification and therefore shows a larger field-of-view than in FIG. 6.

FIG. 6 shows how one sub strip (the area within the dashed box on the left side of the top panel of FIG. 6) is adjusted to form the corrected substrip (bottom panel of FIG. 6). The top panel in FIG. 6 shows an image strip and the left portion of the top panel (surrounded by the dashed box and labeled "Before correction") is a substrip that is processed using the procedures disclosed herein to determine a degree of distortion as well as a correction factor to undo the distortion. The bottom panel of FIG. 6 shows the substrip after its aspect ratio has been adjusted based on the correction factor that was identified using the disclosed procedures. While a horizontal stretching is the only compensation that is performed in this example and thus stretching/compensating in the scanning direction is used in the correction in this example, any combination of stretching or compression of the image, in any direction(s), could be helpful in creating the corrected substrip for a particular use environment. The similar patterns of light and dark areas in the "before" and "after" areas within the red outline should be noted.

FIG. 7 depicts how a smoother, more regular image can be created using the distortion correction described herein, not just in the rotational scanning direction but also in the secondary (e.g. axial) scanning direction. The left panel shows a test or phantom image before application of distortion correction and the right panel shows the same image after distortion corrections. The vertical dimension in each panel is the rotational scanning direction while the horizontal dimension in each panel is the linear scanning direction. As can be seen in the left panel image before distortion correction, many features in the image are misaligned in the horizontal direction, whereas in the image after distortion correction in the right panel the features are more closely aligned left to right. Although this sample is a phantom that was used for demonstration purposes, one of ordinary skill in the art will understand how the distortion correction procedures disclosed herein may be used to help provide more accurate and useful imaging via use of the laser speckle-aided process (e.g., imaging of the inside of a patient's body lumen to detect and/or monitor a lesion).

Figure 8:
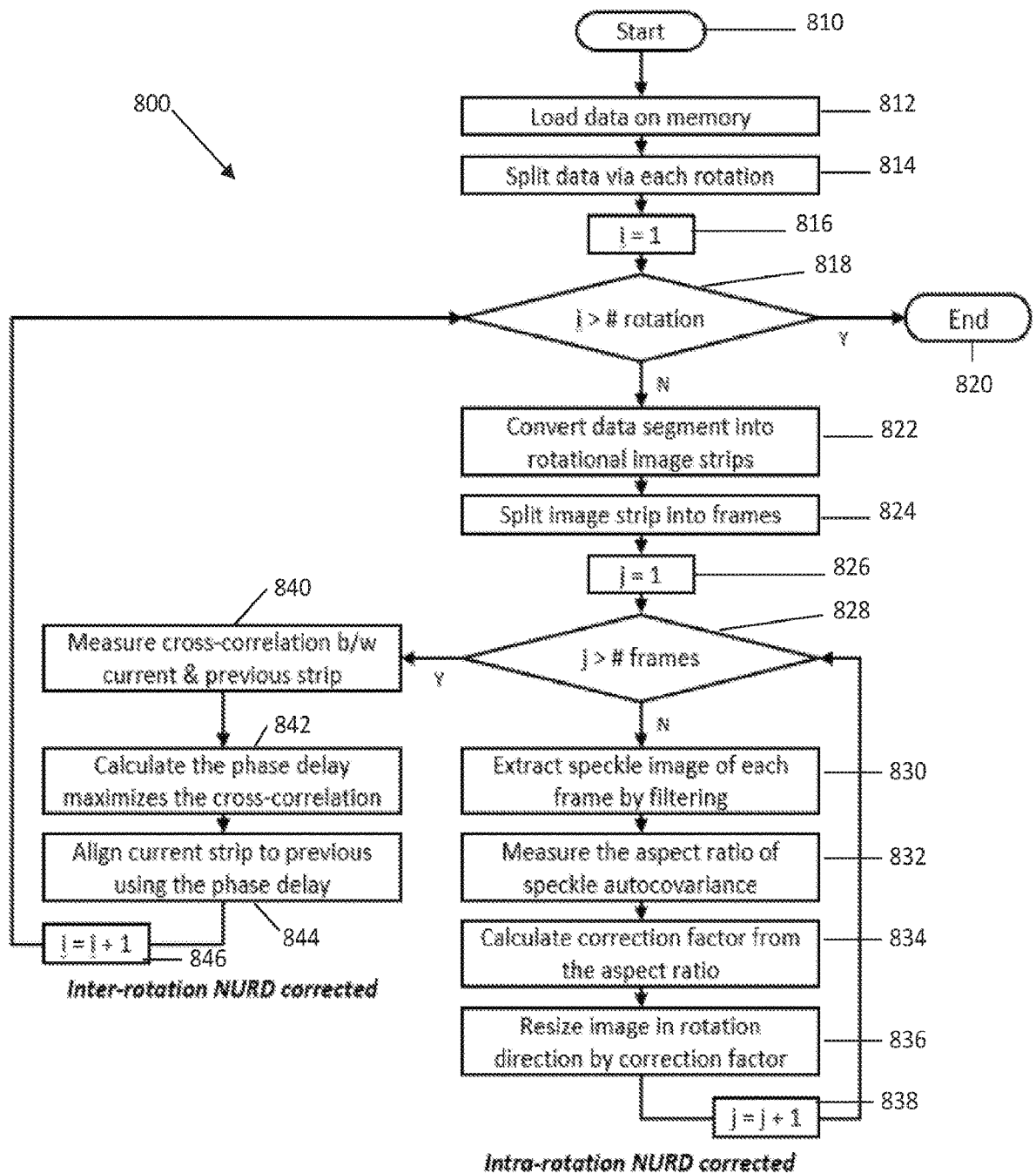
FIG. 8 is a flowchart depicting an example sequence of operation of the present distortion correction algorithm.

FIG. 8 is a flowchart depicting a method 800 for distortion correction according to embodiments of the present invention. At start 810, a step of loading data on memory 812 may be followed by a step of splitting data via each rotation 814, followed by initializing 816 a variable i=1. The method 800 continues 818 until i>#rotations, at which point the method 800 comes to an end 820.

A next step of the method 800 may include converting a data segment into rotational image strips 822. Next, the method 800 may include splitting each image strip into frames, or substrips 824. A variable j may be initialized 826 and set to j=1. The analysis of each sub strip or frame continues 828 until j>#frames. For each substrip or frame, the method 800 may include: extracting a speckle image of each frame by filtering 830; measuring the aspect ratio of speckle autocovariance 832; calculating a correction factor from the aspect ratio 834; and resizing the image in the rotation direction using the correction factor 836. The variable j is incremented 838 so that j=j+1 after each substrip or frame is analyzed and control is returned to step 828 to determine whether j>#frames. The steps of compensating for the distortion of each substrip or frame provides correction for intra-rotation NURD (non-uniform rotational distortion).

When all of the frames of a particular image strip have been analyzed (when j>#frames at step 828), adjustments are made to correct for inter-rotation NURD, i.e. distortion between adjacent image strips. An initial step may include measuring cross-correlation between the current and previous image strips 840; a subsequent step may include calculating a phase delay value which maximizes the cross-correlation 842; and a further step may include aligning the current strip to the previous strip using the phase delay 844. Once this has been completed, the variable i may be incremented 846 so that i=i+1 and control is returned to step 818 to determine whether i>#rotation. Once i is greater than the number of rotations then the method 800 reaches the end 820.

In some embodiments the procedures disclosed herein may be implemented using commercially-available data analysis software; a particular embodiment of such code for the Matlab software package is shown below:

```
% Speckle-based distortion correction
data_ND = [ ];
for s = 1:hori/vert
    ind = 1+(s-1)*vert:s*vert;
    img = data1(:,ind);
    min_int = mean(min(img));
    max_int = mean(max(img));
    avg_int = mean(mean(img));
    med_int = median(median(img));
    imgf = img-wiener2(img,[2 2]); % Wiener filter
    [size_x,size_y] = size(imgf);
    imgf= imresize(imgf,2);
    [HFWHM, VFWHM] = SpeckleSize_gray(imgf);
    mNURD = VFWHM/HFWHM;
    dNURD = mNURD+0.8109...
        -(-451.6*exp(-0.0007511*avg_int)...
        +0.9899*exp(-3.833e-06*avg_int));
    rNURD = 1.619*dNURD^3-3.786*dNURD^2+4.088*dNURD-0.7122; % Custom
    rNURD = max([rNURD 1/vert]); % To prevent factor from being negative
    img_ND = imresize(data1(:,ind),[size_x round(size_y*rNURD)]);
    data_ND = [data_ND,img_ND];
    logdata = [int2str(i),' ',...
        int2str(s),' ',...
        int2str(min_int),' ',...
        int2str(max_int),' ',...
```

```
    int2str(avg_int),' ',...
    int2str(med_int),' ',...
    num2str(HFWHM),' ',...
    num2str(VFWHM),' ',...
    '\r\n'];
  fprintf(logID,logdata);
  % Write in TIF files
  maxint = mean(max(img))/2;
  minint = mean(min(img));
  img = uint16((img-minint)/maxint*(2^16));
  maxint = mean(max(img_ND))/2;
  minint = mean(min(img_ND));
  img_ND = uint16((img_ND-minint)/maxint*(2^16));
  index = ceil(i/Num_steps);
  fname = strcat(bead_folder,c,num2str(index),'-',...
    num2str(s),' (',num2str(VFWHM/HFWHM),')');
  imwrite(img,strcat(fname,'.tif'),'tif');
  fname = strcat(nurd_folder,c,num2str(index),'-',...
    num2str(s),' (',num2str(VFWHM/HFWHM),')_ND');
  imwrite(img_ND,strcat(fname,'.tif'),'tif');
end
data1 = data_ND;
if size(data1,2) < hori/2
  data1 = data0;
end
% Background compensation
hori_cur = size(data1,2);
hori_max = max(hori_max,hori_cur);
dummy = 0; data1_min = min(data1)';
data1_temp = [data1_min(hori_cur-dummy+1:hori_cur);
data1_min;data1_min(1:dummy)];
ylower = smooth(data1_temp,200)';
ylower = ylower(dummy+1:hori_cur+dummy);
comp_BG = repmat(mean(ylower)./ylower,vert,1);
data1 = data1.*comp_BG;
% Image realignment based on crosscorrelation
data1 = circshift(data1,[0 preDiff]);
strip_prev = smooth(mean(data0)-mean(mean(data0)),2000);
strip_curr = smooth(mean(data1)-mean(mean(data1)),2000);
[acor,lag] = xcorr(strip_prev,strip_curr); length_acor = length(acor);
wfunc = normpdf(1:length_acor,(length_acor+1)/2,(length_acor+1)/2/16)';
acor = acor.*wfunc; [~,I] = max(acor); cofactor = (cofactor*(i-1)+I)/i;
lagDiff = lag(I)*(i>1); preDiff = lagDiff;
data1 = circshift(data1,[0 lagDiff]);
data0 = data1;
The following is Matlab code for the SpeckleSize_gray( ) function:
function [HFWHM, VFWHM]=SpeckleSize_gray(SpeckleImg)
M = size(SpeckleImg,1);   %height of area
N = size(SpeckleImg,2);   %width of area
SpeckleImg = double(SpeckleImg);
E = SpeckleImg(1,:);    %creates an array with the values of row 1
s = size(xcov(E));    %finds the size of the autocovariance array
D = zeros(s);    %creates an empty array of size s
D = double(D);    %typecasts the values as doubles
for i = 1:M
  C = SpeckleImg(i,:);
  D = imadd(D,xcov(C,'coeff')); %sums the xcov arrays for all rows into D
end
H0 = D/max(D);    %the finished horizontal product, H, is normalized
sizeH = size(H0,2);
H = H0 (floor(sizeH/2)-5 : floor(sizeH/2)+5);
E1= SpeckleImg(:,1);    %creates an array with the values of column 1
s1= size(xcov(E1));    %finds the size of the autocovariance array
D1 = zeros(s1);    %creates an empty array of size s1
D1 = double(D1);    %typecasts the values as doubles
for j = 1:N
  C1= SpeckleImg(:,j);
  if max(C1)>0
    D1 = D1 + xcov(C1,'coeff');    %sums the xcov arrays for all rows into D1
  end
end
V0 = D1/max(D1);    %the finished vertical product, V, is normalized
sizeV = size(V0);
V = V0(floor(sizeV/2)-5 : floor(sizeV/2)+5);
% H and V are fit to Gaussians and the speckle size is extracted from the fits.
helper1 = 1:size(H,2);
helper2 = 1:size(V);
gauss1 = fittype('gauss1');    %sets up the Gaussian curve fitting
excludeLowH = excludedata(helper1',H','range',[.1,1]);    %excludes the noise from
```

```
outside the speckle
    excludeLowV = excludedata(helper2', V,'range',[.1,1]);
    optionsH = fitoptions(gauss1);
    optionsV = fitoptions(gauss1);
    optionsH.Exclude = excludeLowH;
    options V.Exclude = excludeLowV;
    [HFit, HFitStats] = fit(helper1',H',gauss1, optionsH);
    [VFit, VFitStats] = fit(helper2', V,gauss1, optionsV);
    HFWHM = (2*(HFit.c1)*sqrt(-log(.5/(HFit.a1))));    %FWHM values (Full
width when the fit = .5)
    VFWHM = (2*(VFit.c1)*sqrt(-log(.5/(VFit.a1))));
    HeSquared = ((HFit.c1)*sqrt(-log((.1353353)/(HFit.a1))));    %1/e^2 values (Full
width when the fit = .135...)
    VeSquared = ((VFit.c1)*sqrt(-log((.1353353)/(VFit.a1))));
    end
```

Figure 9:
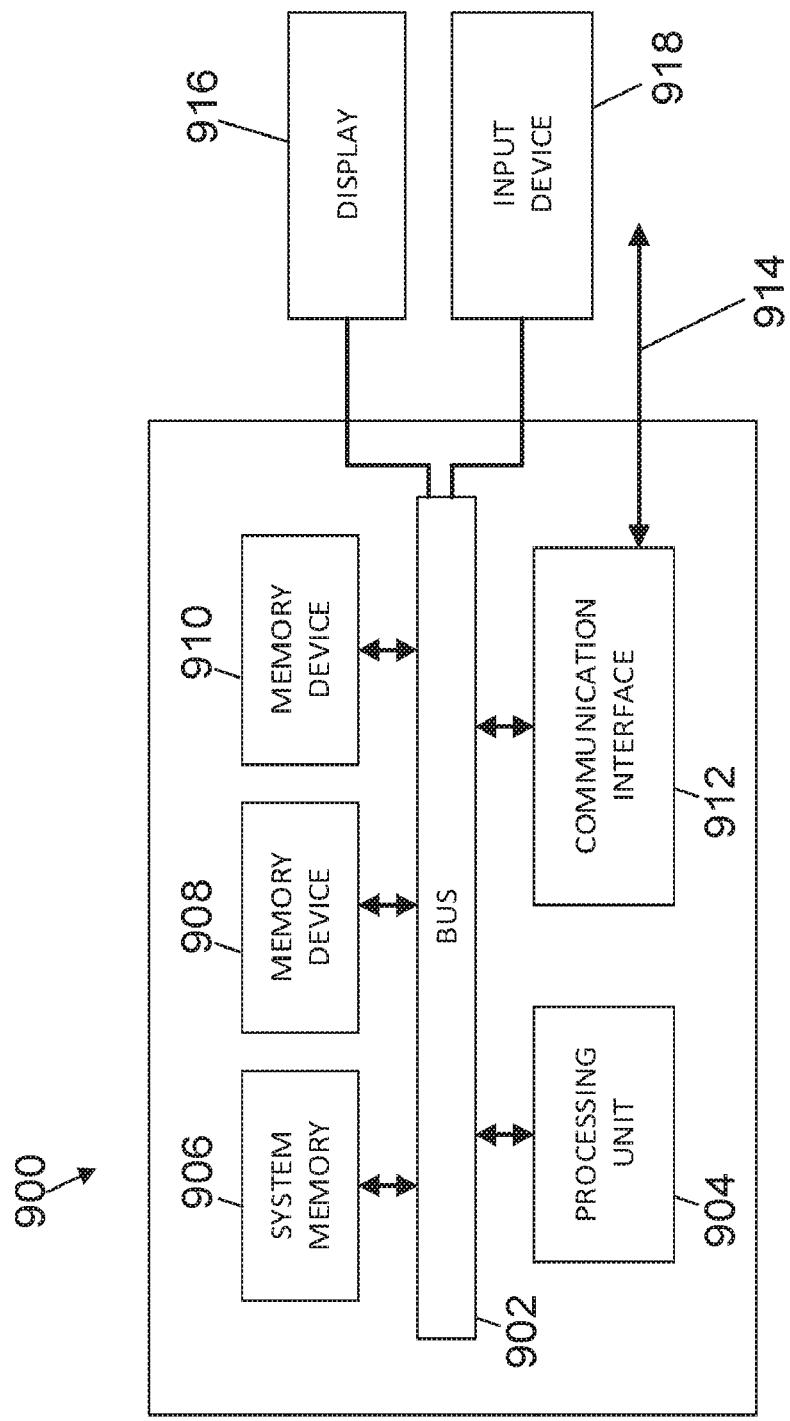
FIG. 9 shows a computer system to implement embodiments of the methods and systems disclosed herein.

FIG. 9 shows a schematic block diagram illustrating an example computer system 900 including hardware components capable of implementing embodiments of the systems and methods disclosed herein for identification and correction of distortion, where the system 900 may include various systems and subsystems. The system 900 can be a personal computer, a laptop computer, a workstation, a computer system, an appliance, an application-specific integrated circuit (ASIC), a server, a server blade center, a server farm, etc. and may be distributed across one or more computing devices.

The system 900 may include a system bus 902, a processing unit 904, a system memory 906, memory devices 908 and 910, a communication interface 912 (e.g., a network interface), a communication link 914, a display 916 (e.g., a video screen) or other output device, and an input device 918 (e.g., a keyboard, mouse, touch screen, touch pad, etc.). The system bus 902 may be in communication with the processing unit 904 and the system memory 906. The additional memory devices 908 and 910, may include various non-transitory storage devices such as a hard disk drive, server, standalone database, or other non-volatile memory, can also be in communication with the system bus 902. The system bus 902 interconnects the processing unit 904, the memory devices 906, 908, 910, the communication interface 912, the display 916, and the input device 918. In some examples, the system bus 902 may also interconnect with one or more additional ports such as a universal serial bus (USB) port, Ethernet port, or other communications mechanism/connection.

The processing unit 904 can be a computing device and can include an application-specific integrated circuit (ASIC) or other processor or microprocessor. The processing unit 904 executes a set of instructions to implement the operations of examples disclosed herein. The processing unit can include a processing core.

The additional memory devices 906, 908, and 910 can store data, programs, instructions, database queries in text or compiled form, and any other information that can be needed to operate a computer. The memories 906, 908, and 910 can be implemented as computer-readable media (integrated or removable) such as a memory card, disk drive, compact disk (CD), or server accessible over a network. In certain examples, the memories 906, 908 and 910 can comprise text, images, video, and/or audio, portions of which can be available in formats comprehensible to human beings.

Additionally or alternatively, the system 900 can access an external data source or query source through the communication interface 912, which can communicate with the system bus 902 and the communication link 914.

In operation, the system 900 can be used to implement one or more parts of the distortion correction in accordance with the present invention. Computer executable logic for implementing portions of the distortion correction reside on one or more of the system memory 906, and the memory devices 908 and 910 in accordance with certain examples. The processing unit 904 executes one or more computer executable instructions originating from the system memory 906 and the memory devices 908 and 910. The term "computer readable medium" as used herein refers to a medium or media that participates in providing instructions to the processing unit 904 for execution.

It will thus be appreciated a computer readable medium is non-transitory and can include multiple discrete media that are operatively connected to the processing unit, for example, via one or more of a local bus or a network connection.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

It should be noted that, as used herein, the term mechanism can encompass hardware, software, firmware, or any suitable combination thereof.

Figure 10:
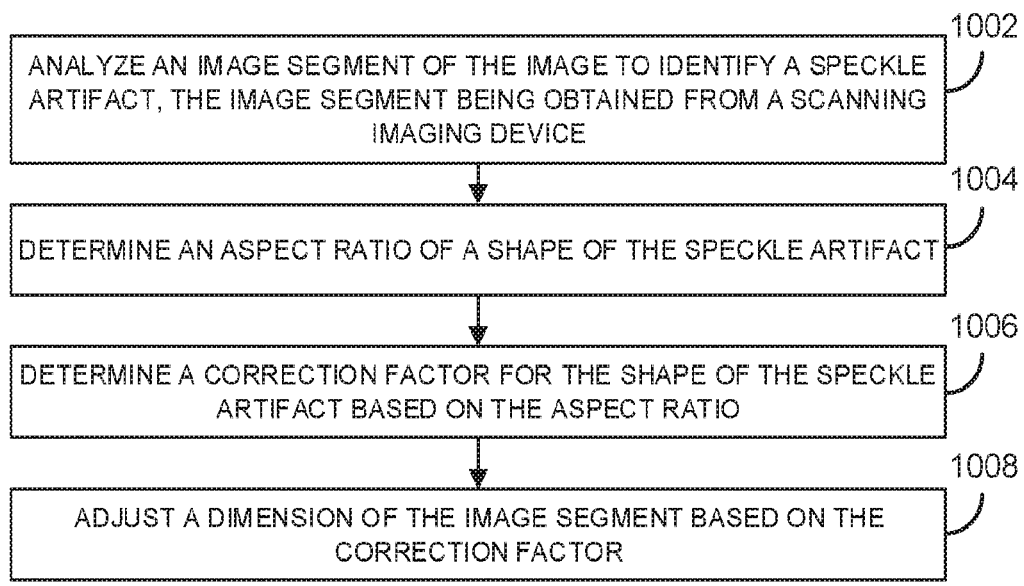
FIG. 10 shows an example of a process for correcting distortion of an image in accordance with some embodiments of the disclosed subject matter.

FIG. 10 shows an example 1000 of a process for correcting distortion of an image in accordance with some embodiments of the disclosed subject matter. As shown in FIG. 10, at 1002, process 1000 can analyze an image segment of the image to identify a speckle artifact, the image segment being obtained from a scanning imaging device. At 1004, process 1000 can determine an aspect ratio of a shape of the speckle artifact. At 1006, process 1000 can determine a correction factor for the shape of the speckle artifact based on the aspect ratio. Finally, at 1008, process 1000 can adjust a dimension of the image segment based on the correction factor.

Figure 11:
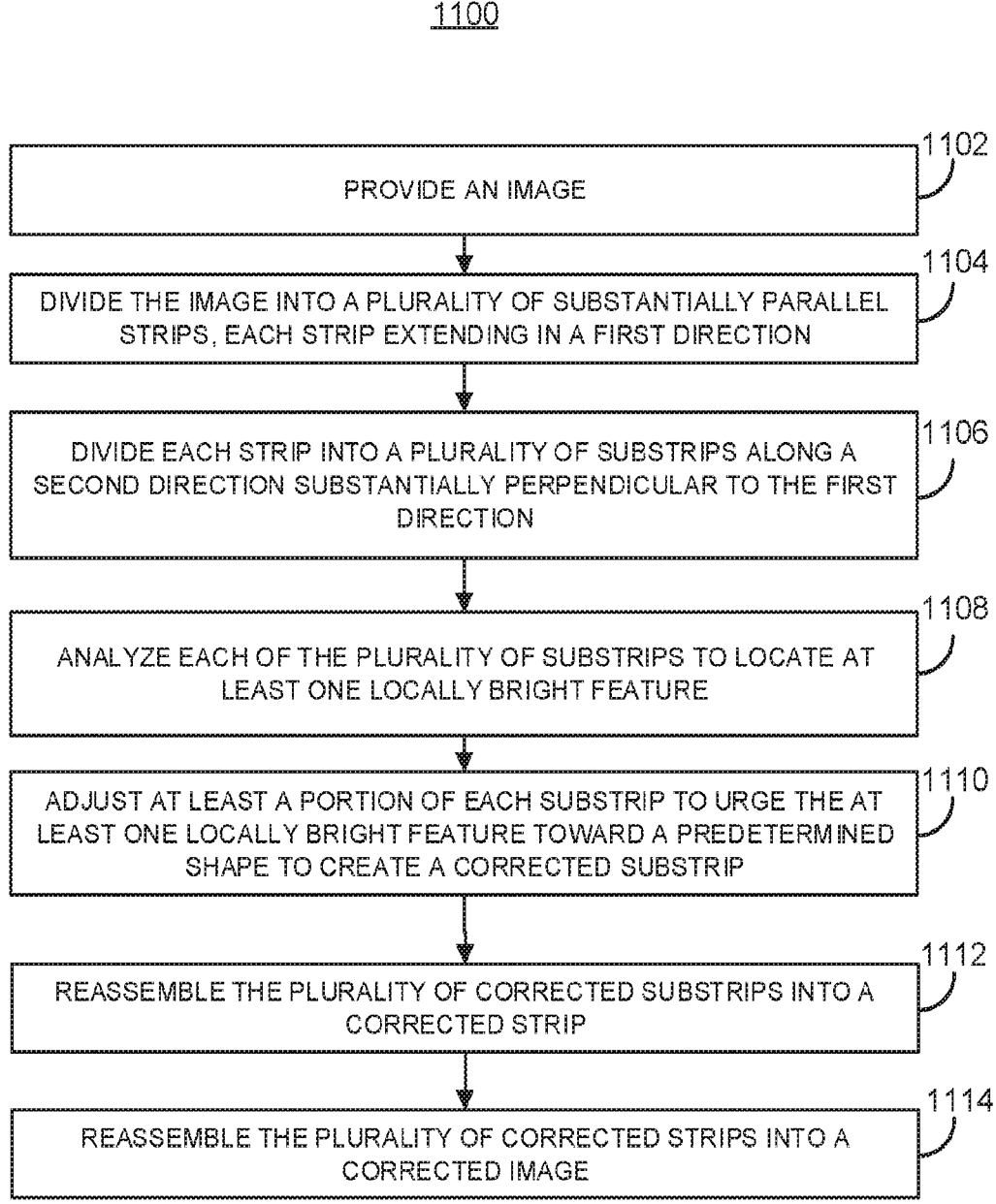
FIG. 11 shows an example of a process for distortion correction in accordance with some embodiments of the disclosed subject matter.

FIG. 11 shows an example 1100 of a process for distortion correction in accordance with some embodiments of the disclosed subject matter. As shown in FIG. 11, at 1102, process 1100 can provide an image. At 1104, process 1100 can divide the image into a plurality of substantially parallel strips, each strip extending in a first direction. At 1106, process 1100 can divide each strip into a plurality of substrips along a second direction substantially perpendicular to the first direction. At 1108, process 1100 can analyze each of the plurality of substrips to locate at least one locally bright feature. At 1110, process 1100 can distort at least a portion of each substrip to urge the local max/min feature toward a predetermined shape and thus create a corrected substrip. At 1112, process 1100 can reassemble the plurality of corrected substrips into a corrected strip. Finally, at 1114, process 1100 can reassemble the plurality of corrected strips into a corrected image.

It should be understood that the above described steps of the processes of FIGS. 10 and 11 can be executed or performed in any order or sequence not limited to the order and sequence shown and described in the figures. Also, some of the above steps of the processes of FIGS. 10 and 11 can be executed or performed substantially simultaneously where appropriate or in parallel to reduce latency and processing times.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

The invention comprises, consists of, or consists essentially of the features described herein, in any combination.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

What is claimed is:

1. A method of correcting distortion of an image, comprising:
    analyzing, by a processor, an image segment of the image to identify a laser speckle artifact,
        the image segment being obtained from a scanning imaging device;
    determining, by the processor, an aspect ratio of a shape of the laser speckle artifact;
    determining, by the processor, a correction factor for the shape of the laser speckle artifact based on the aspect ratio; and
    adjusting, by the processor, a dimension of the image segment based on the correction factor.

2. The method of claim 1, wherein determining the correction factor for the shape of the laser speckle artifact based on the aspect ratio further comprises:
    determining the correction factor based on a polynomial function which relates the aspect ratio to the correction factor.

3. The method of claim 1, wherein the image is obtained from at least one of a rotational scanning device or a linear scanning device.

4. The method of claim 3, wherein the image segment is derived by dividing the image into a plurality of strips,
    wherein each of the plurality of strips is subdivided into a plurality of substrips,
        wherein the image segment comprises one of the plurality of substrips.

5. The method of claim 4, wherein the image is generated by rotational scanning of the sample,
    wherein each of the plurality of strips corresponds to data collected in a rotational scanning direction of the sample.

6. The method of claim 4, further comprising:
    adjusting a dimension of each of the plurality of substrips based on a respective correction factor determined for each of the plurality of substrips,
    reassembling each of the adjusted substrips into a plurality of corrected strips, and
    reassembling the plurality of corrected strips into a corrected image.

7. The method of claim 6, wherein reassembling the plurality of corrected strips into a corrected image further comprises:
    determining a cross-correlation between two adjacent strips of the plurality of corrected substrips,
    calculating a phase delay value which maximizes the cross-correlation, and
    aligning the two adjacent strips based on the calculated phase delay.

8. The method of claim 1, wherein analyzing the image segment to identify the laser speckle artifact further comprises:
    extracting a speckle image of the image segment based on filtering the image segment, and
    wherein determining the aspect ratio of the shape of the laser speckle artifact further comprises:
        determining the aspect ratio based on an autocovariance of the laser speckle artifact in the speckle image.

9. The method of claim 1, wherein the laser speckle artifact is caused by a coherent light source.

10. The method of claim 9, wherein the coherent light source comprises a laser.

11. An apparatus for correcting distortion of an image, comprising:
a processor; and
a memory in communication with the processor having stored thereon a set of instructions which, when executed by the processor, cause the processor to:
analyze an image segment of the image to identify a laser speckle artifact,
the image segment being obtained from a scanning imaging device,
determine an aspect ratio of a shape of the laser speckle artifact,
determine a correction factor for the shape of the laser speckle artifact based on the aspect ratio, and
adjust a dimension of the image segment based on the correction factor.

12. The apparatus of claim 11, wherein the processor, when determining the correction factor for the shape of the laser speckle artifact based on the aspect ratio, is further caused by the instructions to:
determine the correction factor based on a polynomial function which relates the aspect ratio to the correction factor.

13. The apparatus of claim 11, wherein the image from which the image segment is derived is generated by at least one of rotational or linear scanning of a sample.

14. The apparatus of claim 13, wherein the image segment is derived by dividing the image into a plurality of strips,
wherein each of the plurality of strips is subdivided into a plurality of substrips,
wherein the image segment comprises one of the plurality of substrips.

15. The apparatus of claim 14, wherein the image is generated by rotational scanning of the sample,
wherein each of the plurality of strips corresponds to data collected in a rotational scanning direction of the sample.

16. The apparatus of claim 14, wherein the processor is further caused by the instructions to:
adjust a dimension of each of the plurality of substrips based on a determined correction factor for each of the plurality of substrips,
reassemble each of the adjusted substrips into a plurality of corrected strips, and
reassemble the plurality of corrected strips into a corrected image.

17. The apparatus of claim 16, wherein the processor, when reassembling the plurality of corrected strips into a corrected image, is further caused by the instructions to:
determine a cross-correlation between two adjacent strips of the plurality of corrected substrips,
calculate a phase delay value which maximizes the cross-correlation, and
align the two adjacent strips based on the calculated phase delay.

18. The apparatus of claim 11, wherein the processor, when analyzing the image segment to identify the speckle artifact, is further caused by the instructions to:
extract a speckle image of the image segment based on filtering the image segment, and
wherein the processor, when determining the aspect ratio of the shape of the laser speckle artifact, is further caused by the instructions to:
measure the aspect ratio based on an autocovariance of the laser speckle artifact in the speckle image.

19. The apparatus of claim 11, wherein the laser speckle artifact is caused by a coherent light source.

20. The apparatus of claim 19, wherein the coherent light source comprises a laser.

21. A method of distortion correction, the method comprising:
providing an image;
dividing the image into a plurality of substantially parallel strips, each strip extending in a first direction;
dividing each strip into a plurality of substrips along a second direction substantially perpendicular to the first direction;
analyzing each of the plurality of substrips to locate at least one locally bright feature;
adjusting at least a portion of each substrip to urge the at least one locally bright feature toward a predetermined shape to create a corrected substrip;
reassembling the plurality of corrected substrips into a corrected strip; and
reassembling the plurality of corrected strips into a corrected image.

22. The method of claim 21, wherein at least one locally bright feature comprises a laser speckle artifact.

23. The method of claim 21, wherein providing an image includes obtaining an image from a rotational imaging sensor.

24. The method of claim 21, wherein reassembling the plurality of corrected strips into a corrected image further comprises:
performing cross-correlation between pairs of adjacent strips of the plurality of corrected strips,
readjusting relative positions of the pairs of adjacent strips based on performing the cross-correlation, and
reassembling the plurality of corrected substrips into the corrected image based on readjusting the relative positions of the pairs of adjacent strips.

25. An apparatus for correcting distortion of an image, comprising:
a scanning imaging device including a coherent light source,
the scanning imaging device being configured to obtain an image of a sample;
a processor in communication with the scanning imaging device; and
a memory in communication with the processor having stored thereon a set of instructions which, when executed by the processor, cause the processor to:
analyze an image segment of the image to identify a speckle artifact,
determine an aspect ratio of a shape of the speckle artifact,
determine a correction factor for the shape of the speckle artifact based on the aspect ratio, and
adjust a dimension of the image segment based on the correction factor.

26. The apparatus of claim 25, wherein the processor, when determining the correction factor for the shape of the speckle artifact based on the aspect ratio, is further caused by the instructions to:
determine the correction factor based on a polynomial function which relates the aspect ratio to the correction factor.

27. The apparatus of claim 25, wherein the scanning imaging device obtains the image from the sample using at least one of rotational or linear scanning of the sample.

28. The apparatus of claim 27, wherein the image segment is derived by dividing the image into a plurality of strips,
wherein each of the plurality of strips is subdivided into a plurality of substrips, wherein the image segment comprises one of the plurality of substrips.

29. The apparatus of claim 28, wherein the image is obtained by rotational scanning of the sample,
wherein each of the plurality of strips corresponds to data collected in a rotational scanning direction of the sample.

30. The apparatus of claim 28, wherein the processor is further caused by the instructions to:
adjust a dimension of each of the plurality of substrips based on a determined correction factor for each of the plurality of substrips,
reassemble each of the adjusted substrips into a plurality of corrected strips, and
reassemble the plurality of corrected strips into a corrected image.

31. The apparatus of claim 30, wherein the processor, when reassembling the plurality of corrected strips into a corrected image, is further caused by the instructions to:
determine a cross-correlation between two adjacent strips of the plurality of corrected substrips,
calculate a phase delay value which maximizes the cross-correlation, and
align the two adjacent strips based on the calculated phase delay.

32. The apparatus of claim 25, wherein the processor, when analyzing the image segment to identify the speckle artifact, is further caused by the instructions to:
extract a speckle image of the image segment based on filtering the image segment, and
wherein the processor, when determining the aspect ratio of the shape of the speckle artifact, is further caused by the instructions to:
measure the aspect ratio based on an autocovariance of the speckle artifact in the speckle image.

33. The apparatus of claim 25, wherein the speckle artifact is caused by the coherent light source.

34. The apparatus of claim 33, wherein the coherent light source comprises a laser.

* * * * *